United States Patent [19]
Kildal-Brandt et al.

[11] Patent Number: 5,257,212
[45] Date of Patent: Oct. 26, 1993

[54] NORMALIZING ANALYZER SYSTEMS TO A STANDARD ANALYZER

[75] Inventors: Paul A. Kildal-Brandt, Webster; Thomas A. Weber, Rochester; Charles E. Heckler, Rush, all of N.Y.

[73] Assignee: Eastman Kodak Company, Rochester, N.Y.

[21] Appl. No.: 836,694

[22] Filed: Feb. 18, 1992

Related U.S. Application Data

[63] Continuation-in-part of Ser. No. 672,976, Mar. 21, 1991, abandoned.

[51] Int. Cl.$^5$ ............... G06F 15/42; G06F 15/20
[52] U.S. Cl. ............... 364/582; 364/496; 364/571.02
[58] Field of Search ............... 364/582, 570, 496, 497, 364/498, 571.01, 571.02, 571.04, 571.05, 571.07, 571.08; 371/16.2

[56] References Cited

U.S. PATENT DOCUMENTS

| | | | |
|---|---|---|---|
| 4,472,505 | 9/1984 | Manabe et al. | 364/498 |
| 4,587,624 | 5/1986 | Banno | 364/497 X |
| 4,627,014 | 12/1986 | Lo et al. | 364/497 X |
| 4,847,793 | 7/1989 | Cygnarowicz et al. | 364/571.05 X |
| 4,864,842 | 9/1989 | Regimand | 364/571.02 X |
| 4,884,213 | 11/1989 | Iwata et al. | 364/497 |
| 4,947,355 | 8/1990 | Koeman | 364/550 X |
| 5,122,969 | 6/1992 | Seshimoto et al. | 364/497 |

OTHER PUBLICATIONS

*Industrial Applications of Cubic Spline Functions*, N. J. Barosi, Oct. 26, 1973, pp. 3-6, (A Presentation to the 17th Annual Technical Conference of The American Society for Quality Control and The American Statistical Association).

*Splines and Statistics*, Edward J. Wegman and Ian W. Wright, "Journal of the American Statistical Association", Jun. 1983, vol. 78, No. 382, Theory and Methods Section, pp. 351-352.

*Primary Examiner*—Kevin J. Teska
*Attorney, Agent, or Firm*—Dana M. Schmidt

[57] ABSTRACT

There is described a method of calibrating an analyzer in the field, using parameters designed for a "standard" analyzer that may be different from the field analyzer. In this way, it is not necessary to use only certain slide elements of a given chemistry on one analyzer, and certain other slide elements of that same chemistry on another analyzer. Instead, the slide elements are made interchangeable by calibration math which allow the field analyzer to convert its raw response $R_F$ into a response $R_{standard}$ of the selected "standard" analyzer, using the equation $$R_{standard} = B_0 + B_1 \cdot R_F + B_2 \cdot (R_F)^k \qquad (I)$$

The coefficients of this equation are established by comparing, at at least 1 different level of response, $R_F$ against $R_{standard}$, optionally using an intermediate spline function $g_F(R_F)$ in place of $R_F$.

8 Claims, 9 Drawing Sheets

NORMALIZING ANALYZER SYSTEMS TO A STANDARD ANALYZER

RELATED APPLICATIONS

This is a continuation-in-part application of U.S. Ser. No. 672,976, filed Mar. 21, 1991, now abandoned.

FIELD OF THE INVENTION

This invention relates to a method of calibrating a clinical analyzer so that it can be used with slide elements calibrated for use on a drastically different type of analyzer than the one actually used.

BACKGROUND OF THE INVENTION

Certain dried, slide test elements, such as the elements available under the trademark "Ektachem" from Eastman Kodak Company, are capable of use on a variety of different analyzers. These latter include the "Ektachem 700" analyzer and the "Ektachem DT-60" analyzer, both available from Eastman Kodak Co. However, when a test element is used on one type of analyzer, e.g., one that uses one kind of reflectometer, it tends to produce a different correlation between detected response and analyte concentration, than it produces when read on a second type of analyzer, e.g., one that uses a second type of reflectometer. As a result, the correlation between detected response and concentration is different, for any given test element, when read on e.g., the "DT-60" analyzer, compared to its reading on the "Ektachem 700" analyzer.

Such different correlations require that a different calibration curve establishing the correlation, be used for each different kind of analyzer. Different calibration math has to be established for each different type of analyzer. This requires the "proper" type analyzer be used at the factory to determine the calibration, rather than any possible analyzer. Such different calibration curves and the related calibration math have to be "carried" with the test element in question such as by bar coding and/or magnetic disk. Importantly, the correction for such variation is different depending on what kind of analyzer is to be used for detection. As a result, the test elements have to be somehow segregated, using such a system, based on which type of analyzer the elements have been tested on and are destined for. In sum, the test elements have to be paired with a particular type of analyzer, especially if all or some of the calibration math is being passed along with the test elements.

Such pairings or segregation has not been a problem when there are only two basic types of analyzers to choose from, e.g., the "Ektachem 700" type and the "DT-60" type. The reason is that the "DT-60" type elements have already been packaged differently (individually) from the packaging of the "700" types (by cartridge), and the calibration math is passed differently, so that segregation occurs naturally. Where a problem arises is when yet a third type of analyzer is introduced that also packages test elements in a manner that is similar to either of the first two noted above. As a result, the test elements can end up being used on an analyzer for which the test elements bear the wrong calibration math. Keeping track of which test element is to go to what type of analyzer, and thus is to have what calibration math "carried" with it, becomes a horrendous logistics problem.

Therefore, there has been a problem prior to this invention of devising correction factors for the calibration of test elements that will not be different due to which type of analyzer the element ends up being tested on.

It is known to have a correction method that relates an aged test element to that element when fresh, or a lot-varied element of a given assay to a standard element of that assay, when always used on the same analyzer. Such a method is shown for optical density in U.S. Pat. No. 4,884,213. However, that method makes no correction for analyzer-to-analyzer variations, and furthermore incorrectly asserts that the variations that are discussed can always be corrected by a linear relationship.

SUMMARY OF THE INVENTION

The invention is based on the discovery that a relationship exists between how a given test element will perform on one type of analyzer, compared to how it will perform on a standard analyzer, such as on the Kodak "Ektachem 700" TM, hereinafter "E700", analyzer, so that this relationship can be programmed into that one type of analyzer to make its response LOOK like it is a "E700" analyzer response. Once that occurs, correction factors can be sent with all test elements of an assay as though they were all to be tested on the one single type of analyzer, namely (in this case) the "E700" analyzer.

More specifically, there is provided a method of quantitatively determining an analyte in a liquid sample applied to a slide element by measuring in a read station of a field analyzer a response developed in the slide element and correlating the response to an analyte concentration using a calibration curve produced from calibrators having known concentrations, such slide elements being selected from a set of slide elements that all produce the same response in the field analyzer except for deviations due to lot-to-lot variations or aging, the same response being a function of the kind of analyzer used. The method is improved in that the response on the analyzer is corrected substantially to the response that would have been detected on a standard analyzer having one of said calibration curves for correlating the response to an analyte concentration, by the steps of:

a) applying at least one level of the calibrators on at least one of the set of slide elements and reading the response in the standard analyzer, b) repeating step (a) but by reading their response in the field analyzer;

c) correlating the relationship of the different responses in the two analyzers by using the equation (I):

$$R_{standard} = B_0 + B_1 \cdot g_F(R_2) + B_2 g_F(R_F)^k \qquad (I)$$

where $R_{standard}$ is the response detected in the standard analyzer, $R_F$ is the response detected in the field analyzer; $g_F(R_F)$ is a spline function used to transform the responses $R_F$; $B_0$, $B_1$ and $B_2$ are standardizing coefficients; and k is an exponent corresponding to the nonlinearity of the equation, d) applying an unknown patient liquid sample to a slide element selected from the set of slide elements and reading a response in the read station of the field analyzer;

e) ascertaining from the correlation of step (c) what the read response in the field analyzer in step (d) would produce as the corresponding response in the standard analyzer, and f) correlating the ascertained corresponding response to the predicted analyte concentration using the calibration curve of the standard analyzer.

As used herein, "field analyzer" refers to the analyzer used by the customer, which may be the same or a different type as was selected for the standard analyzer.

Thus, it is an advantageous feature of the invention that the calibration of the field analyzer being used is expressed in terms of a single standard analyzer, so that differences introduced by variations in the analyzer type are automatically corrected and the same slide elements can be used in both analyzers even though the calibration math is derived for only a single type of analyzer.

It is a related advantageous feature of the invention that the slide test element bearing a set of calibration parameters is useful in a variety of analyzers having different constructions, rather than just one, and such test elements with their calibration math need not be supplied to only one type of analyzer.

Other advantageous features will become apparent upon reference to the following Description of the Preferred Embodiments when read in light of the attached drawings.

DESCRIPTION OF THE PREFERRED EMBODIMENTS

The invention is hereinafter described in connection with certain preferred embodiments, featuring preferred slide test elements tested in preferred clinical analyzers, wherein calibration math is transmitted by bar codes and/or magnetic disk. In addition, the invention is useful regardless of the form of the test elements, regardless of which types of analyzers are used, and regardless of the mode of transmission of the calibration math, so long as one kind of analyzer is selected as a standard, producing a response against which the response of any other analyzer is compared and corrected as part of the calibration.

The preferred test elements are the slide test elements available from Eastman Kodak Company under the trademark "Ektachem" slides. Such slide elements provide a raw response in the analyzer which is either a reflectance R, an optical density OD where OD=log (1/R), the rate of change of either R, OD, or a transformed OD, or an electrical potential created by a differential measurement of ion concentration in two ion-selective electrodes. Any one of these responses can be calibrated by this invention. (A "transformed OD" is an optical density value obtained through a spline function from raw optical density values to correct for interferences or to convert to other densities, e.g., by using a transform such as the Clapper-Williams transform.)

The preferred analyzers are any of the analyzers available from Eastman Kodak Company under the trademark "Ektachem" analyzer as well as the analyzer available under the tradename "Vettest 8008" from Vettest Corporation.

Any analyzer's reflectometer or detecting station can be used to provide the response $R_{standard}$; that is any analyzer can be the "standard" analyzer. For convenience, due to their common occurrence in industry, the "E700" analyzers available from Eastman Kodak Company have been selected as the "standard" analyzer for this invention.

Any other analyzer used as the field analyzer, is then programmed pursuant to this invention to convert the detected response into the corresponding value that would have been produced on the "E700". Thus, calibration math that is passed along with the slide elements of any given chemistry, are presented as though those slide elements were to be read on an actual "E700" as the field analyzer, even though they may not be. As used herein, "calibration math" includes not only the calibration parameters but also any relevant spline information and concentrations associated with calibrators.

Figure 1:
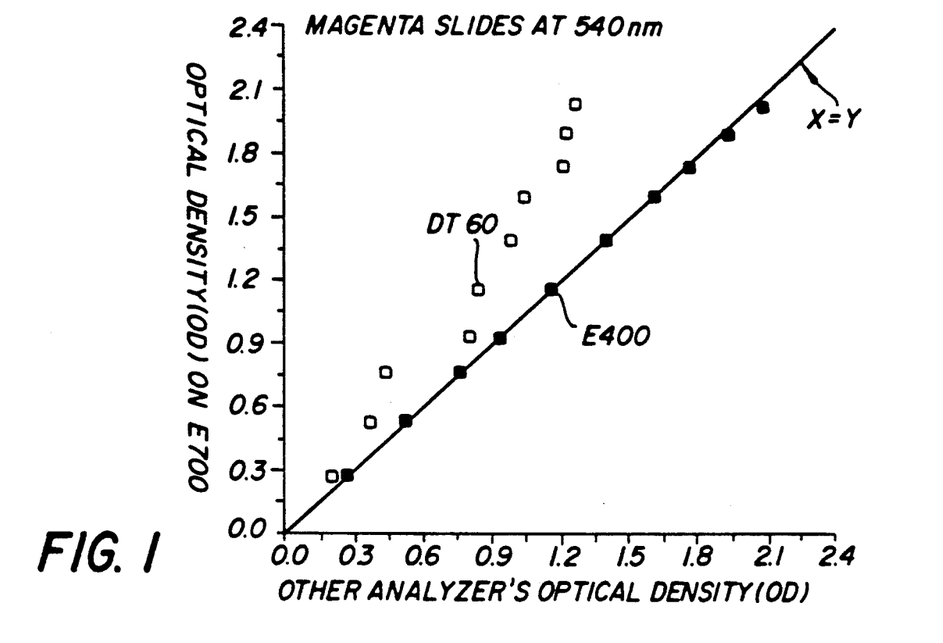
FIG. 1 is a plot of the optical density detected from certain reference elements of known density, using on one hand the standardization analyzer (here, the "E700" analyzer), and, on the other hand, various other analyzers that can be used as field analyzers.

The problem created by different types of analyzers being used to read the same slide elements using only "E700" calibration math, is illustrated in FIG. 1. A series of magenta slides of permanent, differing optical density were read both on the "E700" reflectometer or read station, and then on one of the following reflectometers (or read stations): the reflectometer for the "DT-60" TM analyzer of Eastman Kodak Company, or the reflectometer of the "E400" TM analyzer of Eastman Kodak Company. The X=Y line indicates the substantial identity which is achieved if the "other" analyzer is in fact the "E700" analyzer. Because the results obtained on the "E400" analyzer fall substantially on the X=Y line, it can be assumed, and indeed has been shown, that the "E400" is in fact just another "E700" as far as its calibration math is concerned.

However, the other reflectometer, that of the "DT-60", produces results that deviate significantly from the X=Y line. It can be further shown that the "Vettest 8008", if plotted on FIG. 1, would produce substantial deviation from the X=Y line. A still further example would be a reflectometer identical to that of the "E700" analyzer, except for items such as the incubator for that reflectometer being maintained at a temperature substantially different from that of the "E700" analyzer, or the dispensing station being different, etc.

These deviations are not surprising due to the differences noted. The "Vettest 8008" reflectometer uses LEDs for its visible light and mercury vapor bulbs for UV, that illuminate the slide elements at wavelengths that differ from those used for any given chemistry on the "E700". The "DT-60" reflectometer differs even more in that it uses a contact read station, instead of the non-contact read station of the "E700", created by the fiber optics construction shown, for example, in U.S. Pat. No. 4,302,420 (Jakubowicz et al).

The function then of the invention is to correct the raw reading of, say, the "DT-60" analyzer or the "Vettest 8008" analyzer to the corresponding reading that would have been obtained on the "E700" analyzer. Although this is not as important for the "DT-60" analyzer because its slide elements are packaged differently and its calibration math is passed on different media, as noted above, such packaging or media could change at a future date and be so similar to the packaging and media of the slide elements for the "E700" as to warrant the use of this invention.

Figure 2:
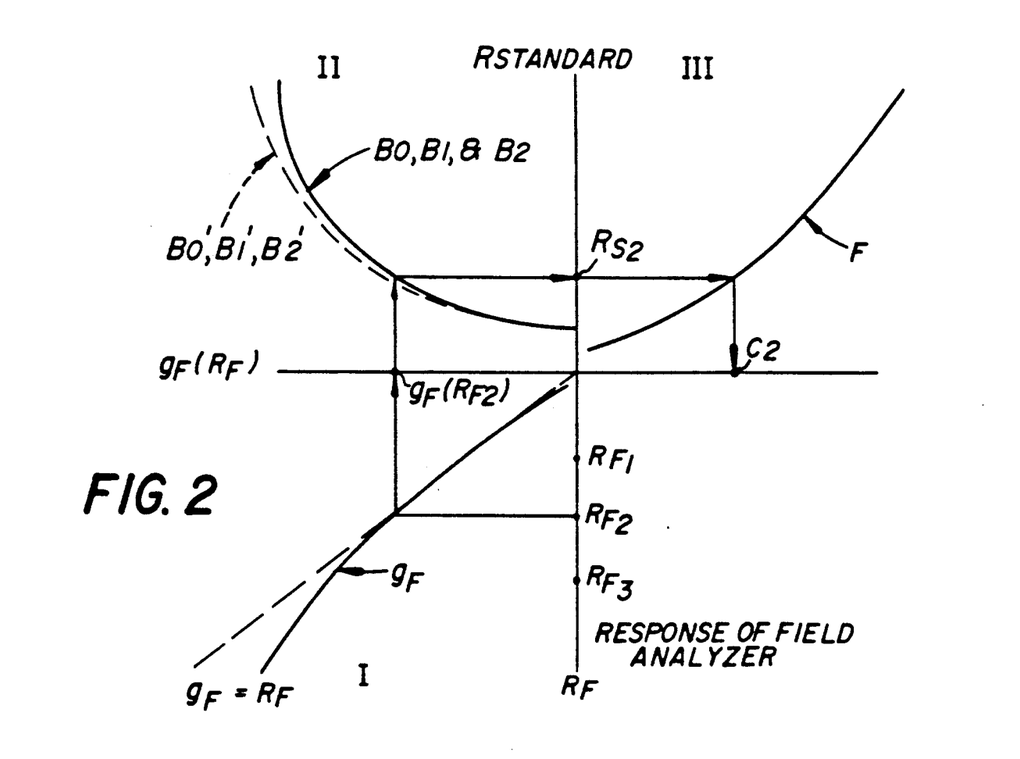
FIG. 2 is a schematic plot that is illustrative of the steps of the invention.

The procedure of the invention is schematically illustrated in FIG. 2. The plot of this figure correlates the response obtained on the field analyzer, $R_F$, to the response $R_{standard}$ obtained or expected on the "standard" analyzer, here, the "E700". Because the $R_{standard}$ values are conventionally correlated to the concentration, as defined by Quadrant III of this plot, the correlation of $R_F$ to $R_{standard}$ will act to convert the field analyzer responses to the concentration predictable as though the analyzer were a "standard" analyzer.

Quadrant II of the plot takes a function $g_F(R_F)$, and correlates that function to $R_{standard}$ by the equation (I) noted above, where it is assumed that k is a value that is either 0 or 2. (If the graph is curved as shown, it is 2.) If, in fact, the raw response $R_F$ is a quadratic function, or a linear function (k=0 and $B_2$=0), of $R_{standard}$, then $g_F(R_F)$ is in fact simply $R_F$ and the curve $g_F$ of Quadrant I becomes the identity line shown in phantom in quadrant I. The only time $g_F$, or Quadrant I, is not unity and must be used, is if k truly is not equal to zero or 2 in equation (I) of Quadrant II. For such occasions, such as the BUN example set forth below, a spline function is generated for the reading $R_F$ to create a $g_F(R_F)$ value that most closely fits the data, as is conventional for spline functions and is described in, for example, *Industrial Applications of Cubic Spline Functions*, by N. J. Barosi, Oct. 26, 1973, pp. 3–6, (A Presentation to the 17th Annual Technical Conference of The American Society for Quality Control and The American Statistical Association), and *Splines and Statistics*, by Edward J. Wegman and Ian W. Wright, "Journal of the American Statistical Association", June 1983, Volume 78, Number 382, Theory and Methods Section, pp. 351–352. Most preferably, the spline is adjusted so as to render the $R_{standard}$ a quadratic function of $g_F(R_F)$. It is then this $g_F(R_F)$ value that can be correlated, quadrant II, to $R_{standard}$ by the quadratic equation (I) where k=2. The coefficients $B_0$, $B_1$ and $B_2$ are the resulting solution of the equation that best fits the data of the plot of $g_F(R_F)$ versus $R_{standard}$.

Ideally, the preceding is handled using fresh slide elements from a standard lot of a given chemistry, the same lot of which is to be used on the field analyzer, also fresh. However, as has been shown in, e.g., the aforesaid U.S. Pat. No. 4,884,213, slight variances can be introduced in the raw response $R_F$ and thus, $g_F(R_F)$, when either a new lot of slide elements for the same chemistry is prepared, or when the slide elements actually tested on the field analyzer are aged. Unfortunately, in most cases the slide elements actually used in the field analyzer will either be aged or from a different lot, or both, and further correction is required. Such correction is obtained, by plotting $R_{variance}$ against $R_{standard}$, where $R_{variance}$ is the response of the aged or lot-varied slide element, and $R_{standard}$ is the response of a fresh slide element from the lot selected to be the "standard" lot, and determining the best fit in accordance with equation (II):

$$R_{standard} = A_0 + A_1 \cdot R_{variance} + A_2 \cdot (R_{variance})^k \quad \text{(II)}$$

It can be shown that, for $R_{variance}$ produced by aged slide elements of the same lot as the standard lot, k of equation (II) will be =0 (and $A_2$=0). For $R_{variance}$ produced by fresh slide elements from a lot different than the standard lot, k of equation (II) is =2. The important factor is, equation (II) is of the same form as equation (I), so that $A_0$, $A_1$ and $A_2$ can be incorporated into $B_0'$, $B_1'$ and $B_2'$, thus correlating for analyzer variation, slide element aging, and lot-to-lot variances, all at once. E.g., the procedure described in the aforesaid U.S. Pat. No. 4,884,213 is useful, except that k=0 and $A_2$=0 only if the variance is due to aging alone, and otherwise k is not equal to 0, but most preferably is equal to 2. Once the $R_{variance}$ corrections have been included in the coefficients of equation (I) of Quadrant II, to provide coefficients $B_0'$, $B_1'$ and $B_2'$, respectively, then the curve may be expected to have shifted to a position such as is shown in phantom.

Once the curve shape of Quadrant II is ascertained, then it is possible to pass on the calibration math obtained from the standard analyzer for any given chemistry to the field analyzer, using the field analyzer $g_F$ and by computing $B_0$, $B_1$ and $B_2$ at the customer site. Thus, each new generation of slide elements need not be tested on all the different analyzer types, nor would separate calibration math for each type of analyzer, and slide elements with such math, be carefully shepardsed only to that type of analyzer. Instead, the new generation and a single set of calibration math becomes applicable to all analyzer types.

The steps of the process of the invention involving reading a response of calibrator liquid of known concentration on a slide element, first on the standard analyzer and then on the field analyzer, is preferably done using three different levels of calibrator liquid. However, one or two levels of calibrators are sufficient if the only difference to be adjusted for is a difference within a single type of field analyzer so as to be just a slope or intercept change or both.

EXAMPLES

The following examples further illustrate the scope of the invention.

In all of these examples, the "standard" analyzer was an "E700" analyzer available from Eastman Kodak Company.

EXAMPLE 1

Glucose Slide Elements in a Vettest 8008 Analyzer

Figure 3:
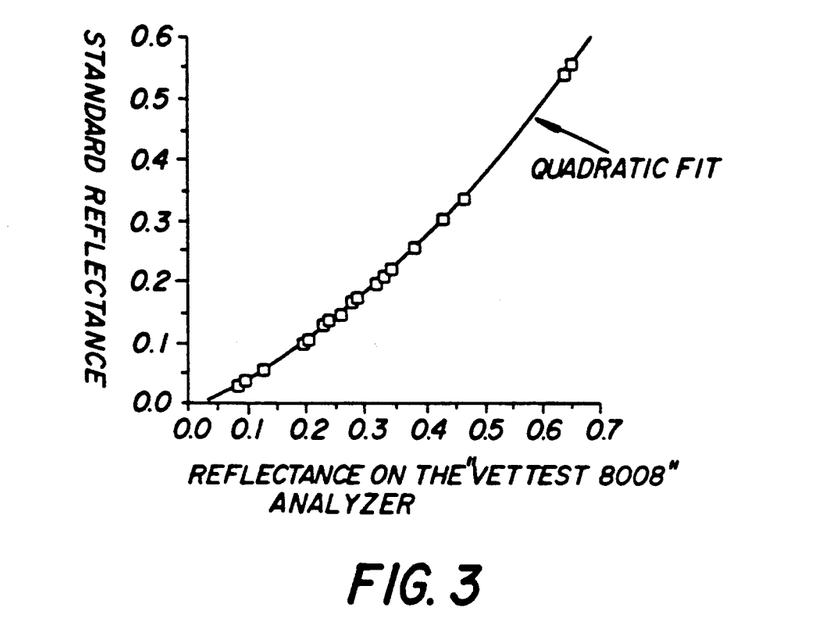
FIG. 3 is a plot of Quadrants I and II of FIG. 2 for a given example of chemistry and a given field analyzer where the $g_F$ function is unity and contributes no correction.

In this example, the field analyzer was a "Vettest 8008" analyzer, and the slide elements were "Ektachem" glucose slide elements from Eastman Kodak Company. A set of 20 fluids with glucose concentrations ranging from 30 to 600 mg/dL were collected. These fluids were spotted onto slides from one lot of glucose test slides and the amount of color formed was read by the two analyzers. The standard responses were plotted versus the responses of the field analyzer and a quadratic polynomial was fit to the data resulting in $B_0$, $B_1$ and $B_2 = -0.1263, 0.46095, 0.62659$, respectively. A graph of the data and the quadratic function can be found in FIG. 3. Standardized responses for the field analyzer were found by evaluating:

$$\text{Standard Response} = B_0 + B_1 \cdot R_F + B_2 \cdot R_F^2$$

The resulting responses are tabulated in Table 1.

TABLE 1

| $R_{standard}$ (E700 Reflectance) | Vettest $R_F$ Refl. | Corrected $R_F$ Refl. | Difference from $R_{standard}$ |
|---|---|---|---|
| .1489 | .2603 | .1505 | +0.0016 |
| .0982 | .1949 | .1014 | +0.0032 |
| .2103 | .3299 | .2087 | -0.0016 |
| .2546 | .3805 | .2549 | +0.0003 |
| .3356 | .4641 | .3384 | +0.0028 |
| .3025 | .4281 | .3014 | -0.0011 |
| .5392 | .6357 | .5376 | -0.0016 |
| .5526 | .6484 | .5538 | +0.0012 |
| .0537 | .1256 | .0553 | +0.0016 |
| .0322 | .0825 | .0297 | -0.0025 |
| .2195 | .3420 | .2195 | NONE |
| .0555 | .1270 | .0562 | +0.0007 |
| .1481 | .2597 | .1500 | +0.0019 |
| .1976 | .3180 | .1983 | +0.0017 |
| .1742 | .2860 | .1712 | -0.0030 |
| .1073 | .2067 | .1098 | +0.0025 |
| .1270 | .2321 | .1287 | +0.0017 |
| .1690 | .2768 | .1637 | -0/0053 |
| .1380 | .2416 | .1359 | -0.0021 |
| .0394 | .0976 | .0384 | -0.0010 |

Figure 4:
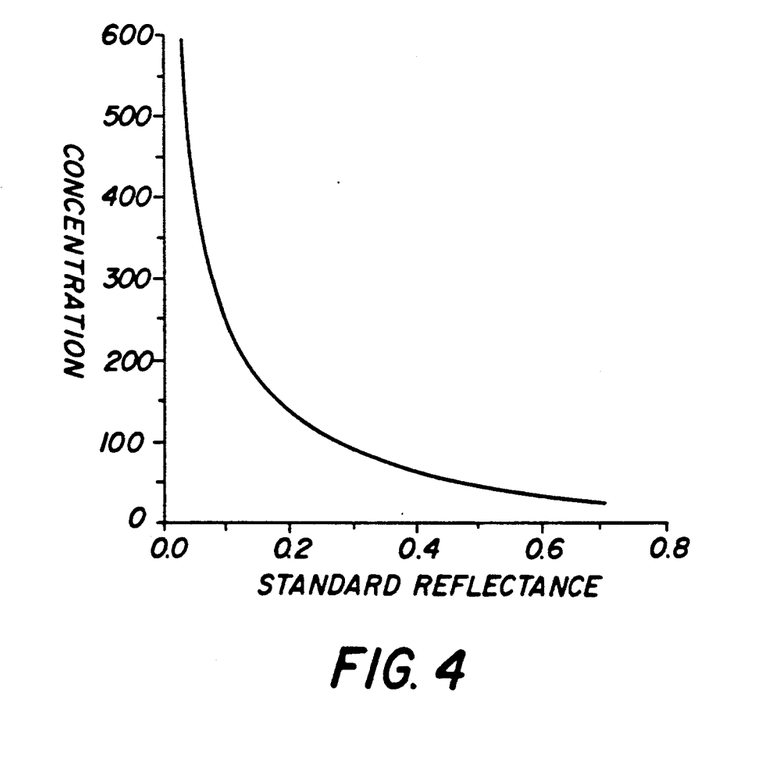
FIG. 4 is a plot of Quadrant III of FIG. 2, for the chemistry of FIG. 3.

Predicted concentrations were found using the known "E700" glucose response to concentration relationship for the lot of glucose slides. A plot of the standard glucose response to concentration relationship for the lot of glucose slides is located in FIG. 4. The predicted concentrations are printed in Table 2. For comparison, the concentration "predicted" from the $R_F$ value, uncorrected, is also shown.

TABLE 2

| E700 Concentration | Concen. from $R_F$ Uncorrected | Response Concen. from $R_F$ Corrected | % Error in Corrected Response Compared to E700 |
|---|---|---|---|
| 180 | 106 | 178 | 1.1 |
| 252 | 142 | 246 | 2.4 |
| 132 | 80 | 133 | 0.8 |
| 108 | 66 | 108 | 0 |
| 78 | 46 | 77 | 1.2 |
| 89 | 55 | 89 | 0 |
| 37 | 27 | 38 | 2.6 |
| 36 | 26 | 38 | 5.6 |
| 85 | 207 | 378 | 1.8 |
| 564 | 287 | 600 | 6.4 |
| 126 | 76 | 126 | 0 |
| 377 | 206 | 374 | 0.8 |
| 181 | 106 | 179 | 1.1 |
| 140 | 84 | 139 | 0.7 |
| 157 | 95 | 160 | 1.9 |
| 235 | 134 | 231 | 1.7 |
| 205 | 119 | 203 | 1.0 |
| 161 | 99 | 166 | 3.1 |
| 192 | 115 | 195 | 1.6 |
| 481 | 253 | 490 | 1.9 |

The % error that remains in Table 2 is not clinically significant to most clinical chemists.

Thus, the calibration of this invention successfully converted the response (here reflectance) of the field analyzer (here, a "Vettest 8008") to the values that would have occurred if such slide elements (here, for glucose) were read on the standard analyzer. Because the equation of quadrant II of FIG. 2 was essentially quadratic in nature, there was no need to use quadrant I in this example. Equivalently, $g_F(R_F) = R_F$ in this example.

EXAMPLE 2

BUN Slide Elements In a Vettest 8008 Analyzer

Figure 5:
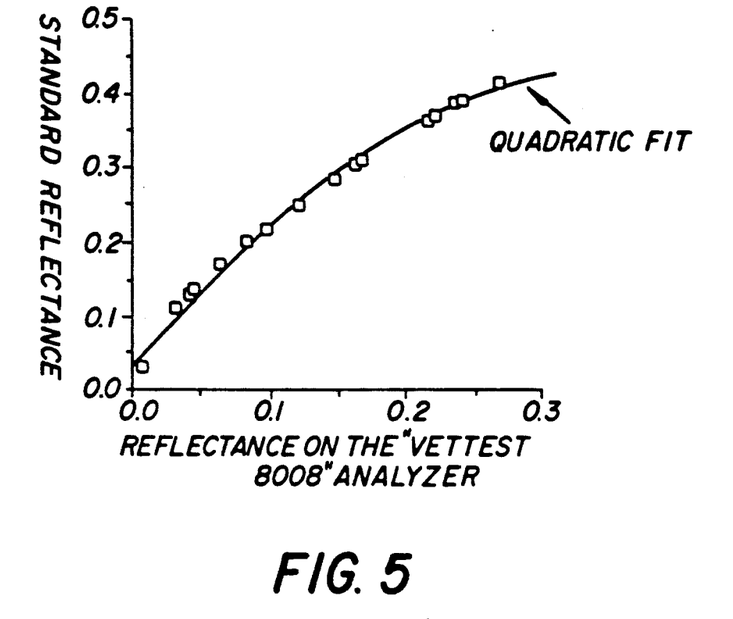
FIG. 5 is a plot similar to FIG. 3, but for a different chemistry.

The same analyzers were used in this test as in Example 1. A set of 20 fluids with BUN concentrations ranging from 10 to 90 mg/dL were collected. These fluids were spotted onto slides from one lot of BUN test slides and the amount of color formed was read by the two analyzers. The standard responses were plotted versus the responses of the field analyzer and a quadratic polynomial was fitted to the data resulting in $B_0$, $B_1$, $B_2 = 0.02845, 2.2517, -3.0861$, respectively. A graph of the data and the quadratic function can be found in FIG. 5. Standardized responses for the field analyzer were found by evaluating:

$$\text{Standard Response} = B_0 + B_1 \cdot R_F + B_2 \cdot R_F^2$$

for each $R_F$ (i.e., response on the field analyzer). The resulting responses are tabulated in Table 3.

TABLE 3

| $R_{standard}$ E700 Reflectance | Vettest Refl. | Corrected $R_F$ Refl. |
|---|---|---|
| .2013 | .0845 | .1967 |
| .3654 | .2153 | .3701 |
| .3899 | .2344 | .3867 |
| .2881 | .1455 | .2908 |
| .3127 | .1668 | .3182 |
| .2197 | .0958 | .2158 |
| .1298 | .0429 | .1193 |
| .3917 | .2392 | .3905 |
| .2525 | .1207 | .2553 |
| .3082 | .1622 | .3125 |
| .3749 | .2199 | .3744 |
| .4162 | .2668 | .4095 |
| .1722 | .0652 | .1620 |
| .1137 | .0324 | .0982 |
| .0319 | .0065 | .0430 |
| .0342 | .0068 | .0435 |

TABLE 3-continued

| $R_{standard}$ E700 Reflectance | Vettest Refl. | Corrected $R_F$ Refl. |
|---|---|---|
| .0312 | .0066 | .0431 |
| .1373 | .0462 | .1258 |
| .2871 | .1479 | .2940 |
| .2864 | .1488 | .2952 |

From this, predicted concentrations were found using the known "E700" BUN response to concentration relationship for the lot of BUN slides. The predicted concentrations are printed in Table 4, and for comparison, a predicted concentration from $R_F$ uncorrected, is also shown.

TABLE 4

| Concen. from E700 Concentration | Concen. from $R_F$ Uncorrected | $R_F$ Corrected |
|---|---|---|
| 30 | 58 | 31 |
| 14 | 28 | 13 |
| 12 | 26 | 12 |
| 20 | 40 | 20 |
| 18 | 36 | 17 |
| 28 | 54 | 28 |
| 44 | 80 | 47 |
| 12 | 25 | 12 |
| 24 | 46 | 23 |
| 18 | 37 | 18 |
| 13 | 28 | 13 |
| 11 | 22 | 11 |
| 35 | 66 | 37 |
| 48 | 89 | 53 |
| 89 | 135 | 80 |
| 87 | 134 | 79 |
| 90 | 135 | 80 |
| 42 | 77 | 45 |
| 20 | 40 | 19 |
| 20 | 40 | 19 |

Although the concentration from $R_F$, corrected, is close to the "true" result shown in the left hand column, there is substantial deviation for concentrations above 45. This means that the equation (I) of quadrant II that best fits the raw reflectance data is not truly quadratic.

Figure 6:
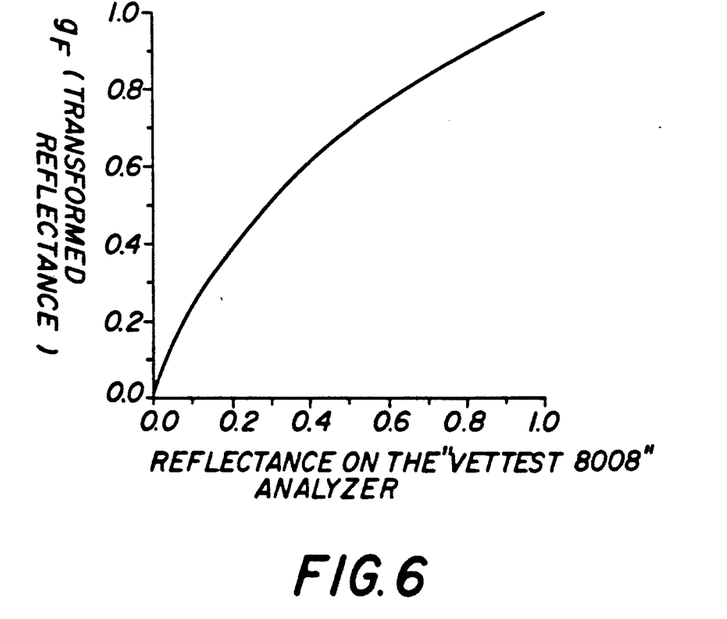
FIG. 6 is a plot corresponding to the chemistry of FIG. 5 using, however, a $g_F$ correction provided in the manner indicated in Quadrant I.

Hence, a $g_F$ function was found to remove the non-quadratic response differences that existed between the "E700" and the field analyzer. The $g_F$ function was represented as the following cubic spline:

| X-Value | Y-Value | 2nd Derivative |
|---|---|---|
| 0.0 | 0.0 | 0.0 |
| .02 | .067684 | −31.76737 |
| .12 | .275344 | −2.2153 |
| 1.0 | 1.0 | 0.0 | to be used to provide a curve such as forms quadrant I of FIG. 2. More specifically, the relation of $R_F$ of Table 3, and this $g_F(R_F)$ is shown in FIG. 6.

Figure 7:
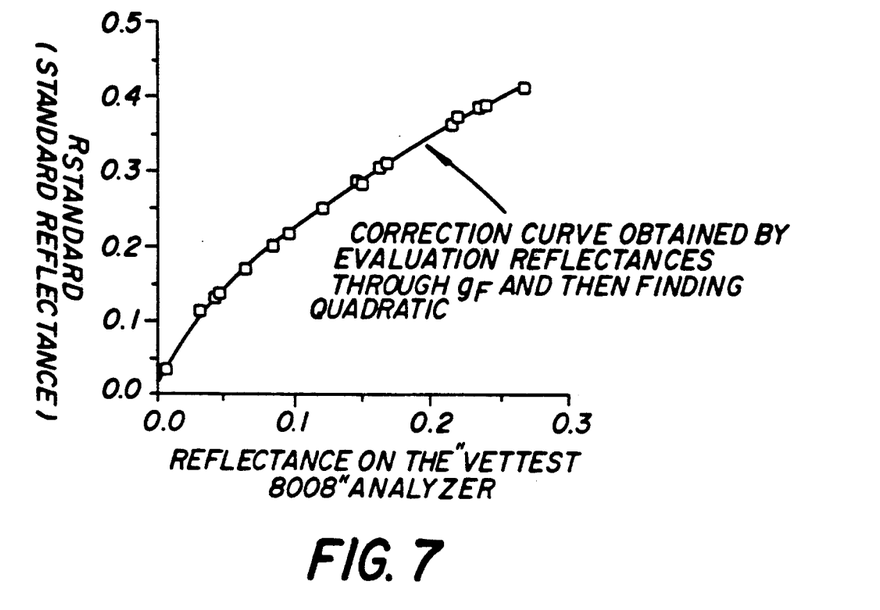
FIG. 7 is a plot similar to that of FIG. 5, after the correction of FIG. 6 has been applied.

The standard responses, $R_{standard}$, were plotted versus the responses of the field analyzer. The field analyzer responses were evaluated through $g_F$ and then a quadratic polynomial, which changed transformed field analyzer responses to standard responses, was found. This resulted in $B_0$, $B_1$, $B_2 = 0.013317$, $0.881242$, $-0.029543$, respectively. A graph of the data and the correction curve can be found in FIG. 7. Standardized responses for the field analyzer were found by evaluating:

$$\text{Standard Response} = B_0 + B_1 \cdot g_F(R_F) + B_2 \cdot g_F(R_F)^2$$

for each $R_F$ (i.e., response on the field analyzer). The resulting responses are tabulated in Table 5.

TABLE 5

| $R_{standard}$ E700 Reflectance | Vettest $R_F$ Refl. | $g_F(R_F)$ | Corrected Reflectance from $g_F(R_F)$ |
|---|---|---|---|
| .2013 | .0845 | .2195 | .2053 |
| .3654 | .2153 | .4060 | .3662 |
| .3899 | .2344 | .4300 | .3868 |
| .2881 | .1455 | .3122 | .2856 |
| .3127 | .1668 | .3419 | .3112 |
| .2197 | .0958 | .2383 | .2217 |
| .1298 | .0429 | .1325 | .1296 |
| .3917 | .2392 | .4359 | .3919 |
| .2525 | .1207 | .2764 | .2546 |
| .3082 | .1622 | .3356 | .3057 |
| .3749 | .2199 | .4119 | .3713 |
| .4162 | .2668 | .4960 | .4201 |
| .1722 | .0652 | .1831 | .1737 |
| .1137 | .0324 | .1048 | .1053 |
| .0319 | .0065 | .0227 | .0333 |
| .0342 | .0068 | .0235 | .0340 |
| .0312 | .0066 | .0228 | .0334 |
| .1373 | .0462 | .1407 | .1367 |
| .2871 | .1479 | .3156 | .2885 |
| .2864 | .1488 | .3169 | .2896 |

Figure 8:
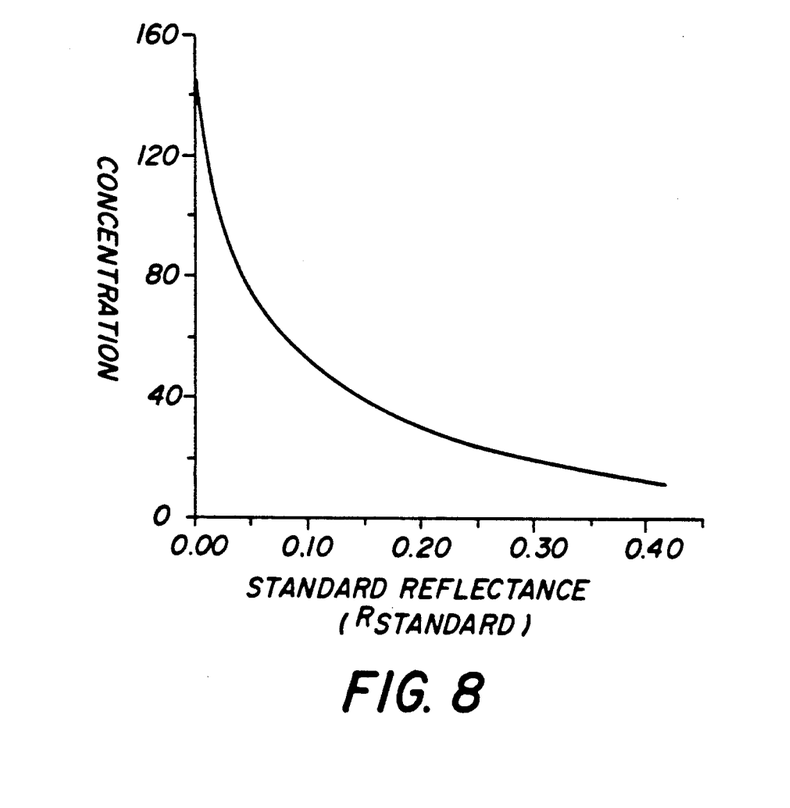
FIG. 8 is a plot of Quadrant III of FIG. 2, for the chemistry and results obtained from FIG. 7.

Predicted concentrations were found using the known "E700" BUN response to concentration relationship for the lot of BUN slides. A plot of the standard BUN response to concentration relationship for the lot of BUN slides is located in FIG. 8. The predicted concentrations are printed in Table 6. For comparison, a predicted concentration from $R_F$, uncorrected, is also shown.

TABLE 6

| E700 Concentration | Concen. from $R_F$ Uncorrected | Concen. from $g_F(R_F)$ | % Error Compared to $C_{standard}$ |
|---|---|---|---|
| 30 | 58 | 30 | 0 |
| 14 | 28 | 14 | 0 |
| 12 | 26 | 12 | 0 |
| 20 | 40 | 20 | 0 |
| 18 | 36 | 18 | 0 |
| 28 | 54 | 27 | 3.7 |
| 44 | 80 | 44 | 0 |
| 12 | 25 | 12˙ | 0 |
| 24 | 46 | 23 | 4.2 |
| 18 | 37 | 18 | 0 |
| 13 | 28 | 13 | 0 |
| 11 | 22 | 10 | 9.1 |
| 35 | 66 | 35 | 0 |
| 48 | 89 | 51 | 6.3 |
| 89 | 135 | 88 | 1.1 |
| 87 | 134 | 87 | 0 |
| 90 | 135 | 88 | 2.2 |
| 42 | 77 | 42 | 0 |
| 20 | 40 | 20 | 0 |
| 20 | 40 | 20 | 0 |

It is clear from Table 6 that the $g_F$ function together with the quadratic correction effectively standardizes the responses of the field analyzer to the "E700" analyzer.

EXAMPLE 3

Glucose Slide Elements in a DT-60 Analyzer

Figure 9:
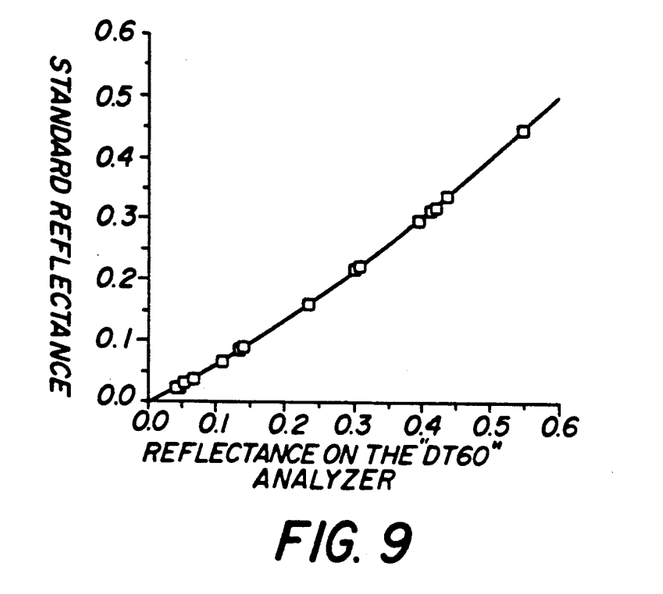
FIG. 9 is a plot similar to that of FIG. 3, but for yet another field analyzer.

The procedure of Example 1 was repeated, except that the field analyzer was a "DT-60" analyzer from Eastman Kodak Company. A set of 19 fluids with glucose concentrations ranging from 48 to 710 mg/dL were collected. These fluids were spotted onto slides from one lot of glucose test slides and the amount of color formed was read by the two analyzers. The standard responses were plotted versus the responses of the field analyzer and a quadratic polynomial was fit to the data resulting in ($B_0$, $B_1$, $B_2 = -0.005724$, $0.602386$, $0.412017$). A graph of the data and the quadratic function can be found in FIG. 9. Standardized responses for the field analyzer were found by evaluating:

Standard Response = $R_0 + B_1 \cdot R_F + B_2 R_F^2$ for each $R_F$ (i.e., response on the field analyzer). The resulting responses are tabulated in Table 7.

TABLE 7

| E700 Reflectance | DT60 Refl. | Corrected $R_F$ (DT60) Refl. |
| --- | --- | --- |
| .4482 | .5487 | .4488 |
| .0828 | .1348 | .0830 |
| .0298 | .0554 | .0289 |
| .3233 | .4238 | .3236 |
| .3108 | .4100 | .3105 |
| .3368 | .4359 | .3351 |
| .3190 | .4207 | .3206 |
| .2231 | .3086 | .2194 |
| .2984 | .3978 | .2991 |
| .1593 | .2370 | .1602 |
| .2141 | .3019 | .2137 |
| .0655 | .1132 | .0677 |
| .0668 | .1134 | .0679 |
| .0877 | .1420 | .0881 |
| .0372 | .0705 | .0388 |
| .0375 | .0700 | .0385 |
| .0350 | .0658 | .0357 |
| .0225 | .0411 | .0198 |
| .0255 | .0473 | .0237 |

Figure 10:
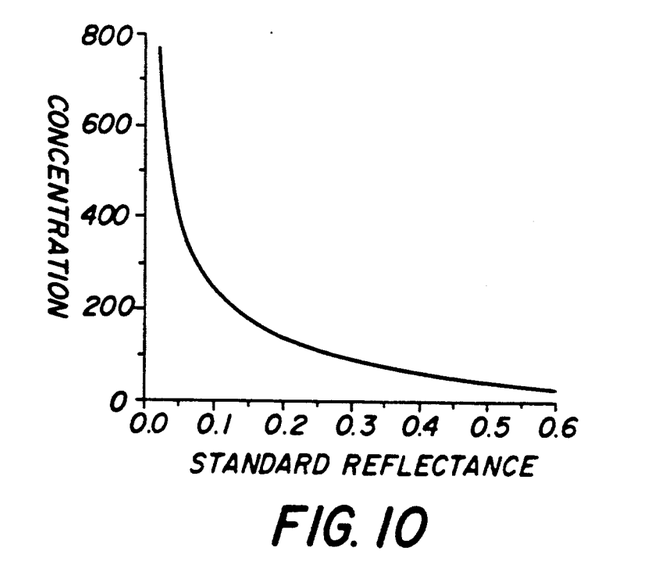
FIG. 10 is a plot similar to that of FIG. 4, for the analyzer of FIG. 9.

Predicted concentrations were found using the known "E700" glucose response to concentration relationship for the lot of glucose slides. A plot of the standard glucose response to concentration relationship for this lot of glucose slides is located in FIG. 10. The predicted concentrations are printed in Table 8. For comparison, the concentration "predicted" from the $R_F$ value, uncorrected, is also shown.

TABLE 8

| E700 Concentration | Concen. from $R_F$ Uncorrected | Concen. from $R_F$ (Corrected) |
| --- | --- | --- |
| 48 | 28 | 48 |
| 286 | 197 | 286 |
| 580 | 375 | 594 |
| 81 | 54 | 81 |
| 85 | 57 | 85 |
| 76 | 51 | 77 |
| 82 | 55 | 82 |
| 123 | 86 | 125 |
| 89 | 60 | 89 |
| 170 | 116 | 169 |
| 129 | 88 | 129 |
| 335 | 227 | 328 |
| 331 | 227 | 327 |
| 275 | 188 | 274 |
| 493 | 319 | 478 |
| 490 | 321 | 481 |
| 516 | 334 | 508 |
| 711 | 459 | 774 |
| 652 | 417 | 686 |

This, the calibration of this invention successfully converted the response (here reflectance) of the field analyzer (here, an "Ektachem DT60") to the values that would have occurred if such slide elements (here, for glucose) were read on the standard analyzer. Because the equation of quadrant II of FIG. 2 was essentially quadratic in nature, there was no need to use quadrant I in this example. Equivalently, $g_F(R_F) = R_F$ in this example.

EXAMPLE 4

Rate Assay Slide Elements in a "Vettest 8008" Analyzer

Figure 11:
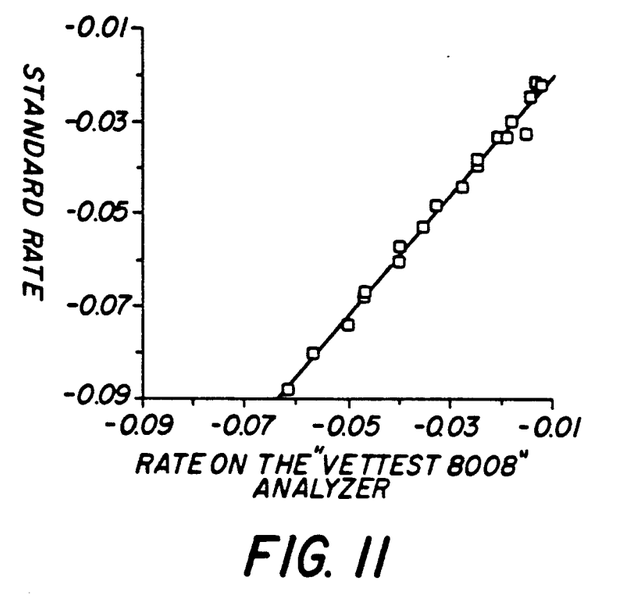
FIG. 11 is a plot similar to that of FIG. 3, illustrating the invention when using a rate assay.

The procedure of Example 1 was repeated, except that the field analyzer was a "Vettest 8008" and the slide elements were "Ektachem" LDH slides from Eastman Kodak Company. A set of 20 fluids with LDH activities ranging from 182 to 1420 U/L were collected. These fluids were spotted onto slides from one lot of LDH test slides and the rate of change of optical density (OD) was read by the two analyzers. The standard responses were plotted versus the responses of the field analyzer and a quadratic polynomial was fit to the data resulting in ($B_0$, $B_1$, $B_2 = -0.00811$, $1.20522$, $-1.051568$). A graph of the data and the quadratic function can be found in FIG. 11. Standardized responses for the field analyzer were found by evaluating:

Standard Response = $B_0 + B_1 \cdot R_F + B_2 \cdot R_F^2$ for each $R_F$ (i.e., response on the field analyzer). The resulting responses are tabulated in Table 9.

TABLE 9

| E700 Rate | Vettest Rate | Corrected Vettest Rate |
| --- | --- | --- |
| −.0330 | −.0202 | −.0331 |
| −.0525 | −.0355 | −.0527 |
| −.0217 | −.0121 | −.0229 |
| −.0434 | −.0275 | −.0424 |
| −.0326 | −.0189 | −.0315 |
| −.0677 | −.0470 | −.0682 |
| −.0733 | −.0499 | −.0720 |
| −.0389 | −.0244 | −.0384 |
| −.0593 | −.0404 | −.0592 |
| −.0321 | −.0153 | −.0269 |
| −.0376 | −.0241 | −.0381 |
| −.0668 | −.0466 | −.0675 |
| −.0480 | −.0322 | −.0485 |
| −.0294 | −.0174 | −.0295 |
| −.0294 | −.0176 | −.0298 |
| −.0802 | −.0562 | −.0807 |
| −.0570 | −.0396 | −.0582 |
| −.0882 | −.0613 | −.0876 |
| −.0237 | −.0138 | −.0250 |
| −.0216 | −.0130 | −.0241 |

Figure 12:
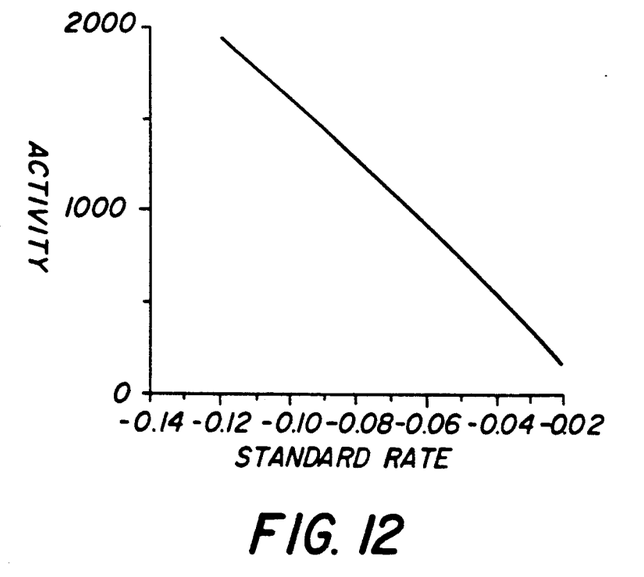
FIG. 12 is a plot of Quadrant III of FIG. 2, but for the rate assay of FIG. 11.

Predicted activities were found using the known "E700" LDH response to activity relationship for the lot of LDH slides. A plot of the standard LDH response to activity relationship for this lot of LDH slides is located in FIG. 12. The predicted activities are printed in table 10. For comparison, the activity "predicted" from the $R_F$ value, uncorrected, is also shown.

TABLE 10

| E700 Activity | Uncorrected Vettest Activity | Corrected Vettest Activity |
| --- | --- | --- |
| 418 | 154 | 419 |
| 791 | 466 | 796 |
| 184 | −23 | 210 |
| 620 | 307 | 602 |
| 408 | 127 | 387 |
| 1065 | 689 | 1074 |
| 1163 | 743 | 1141 |
| 533 | 241 | 523 |
| 916 | 562 | 915 |
| 398 | 48 | 294 |
| 509 | 236 | 517 |

TABLE 10-continued

| E700 Activity | Uncorrected Vettest Activity | Corrected Vettest Activity |
|---|---|---|
| 1050 | 681 | 1063 |
| 708 | 402 | 717 |
| 345 | 93 | 346 |
| 344 | 99 | 353 |
| 1283 | 860 | 1291 |
| 875 | 547 | 895 |
| 1419 | 951 | 1409 |
| 227 | 15 | 254 |
| 183 | −1 | 235 |

Thus, the calibration of this invention successfully converted the response (here rate) of the field analyzer (here, a "Vettest 8008") to the values that would have occurred if such slide elements (here, for LDH) were read on the standard analyzer. Because the equation of quadrant II of FIG. 2 was essentially quadratic in nature, there was no need to use quadrant I in this example. Equivalently, $g_F(R_F)=R_F$ in this example.

FACTORY CALIBRATION

It is not necessary that the second and third steps of this invention (of reading the field analyzer response and establishing the coefficients of equation no. (I)) be done at the field site, called "wet calibration", although this is one use of the invention. In addition, it can all be done at the manufacturing site of the field analyzer. In many cases we have found that factory calibration results are comparable to results obtained using conventional wet calibration. (During such conventional wet calibration, the analyzer and slide elements are characterized at the customer site by reading the slide response of a number of calibrator fluids on the site's analyzer. This information is then used to define the relationship between analyte concentration and slide response for all patient samples on the site's analyzer.)

Figure 13:
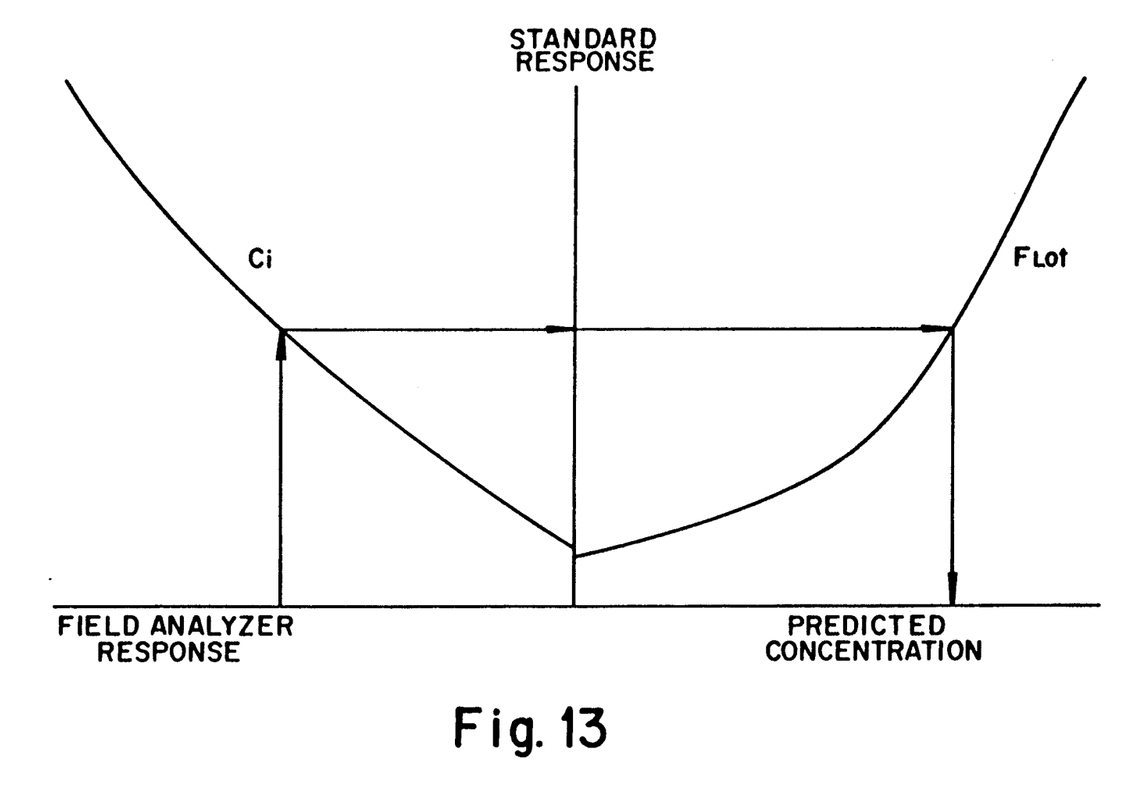
FIG. 13 is a plot similar to that of FIG. 2, but illustrating an alternative embodiment, namely factory calibration.

FIG. 13 is a graphical representation of the use of the invention in factory calibration. The left hand quadrant depicts the analyzer characterization and the right hand quadrant depicts the test element characterization. In factory calibration, equation (I) is a correction of the field analyzer response of whatever type (Dr, rate or mv) to the standard response. Conveniently, the quadratic form of equation (I) above is used, e.g., $$Response_{standard}=B_0+B_1 \cdot R_f+B_2 \cdot R_F^2$$

where $R_F$ is the response of the chemistry on the field analyzer and $B_0$, $B_1$, and $B_2$ are the coefficients of the quadratic correction found in the factory or manufacturing site for the field analyzer and chemistry. The same coefficients could be used for multiple chemistries.

The curve $F_{Lot}$ is found by calibrating the test element on the analyzer chosen as the standard analyzer for factory calibration using the test element's wet calibration model. The mathematical relationship of this curve is then passed on to the customer in suitable coded form, e.g., a bar code associated with the test element.

The following examples demonstrate the effectiveness of this factory calibration technique.

EXAMPLE 5

Factory Calibration of Glucose Colorimetric Slide Element

This test used the following:

Nine "E700" TM analyzers manufactured by Eastman Kodak Co., which were intentionally varied, e.g., by altering the volume to be metered or by changing the position of the spotted liquid on the test element from the optimum, to cause analyzer response differences; "Ektachem" TM elements from Eastman Kodak Co., from five different glucose coatings; three calibrator fluids; three control fluids; and two patient pools.

Eight repetitions of each fluid were run on every analyzer/coating combination for a total of 360 (8×5×9) repetitions of each fluid.

CONTROL

Figure 14:
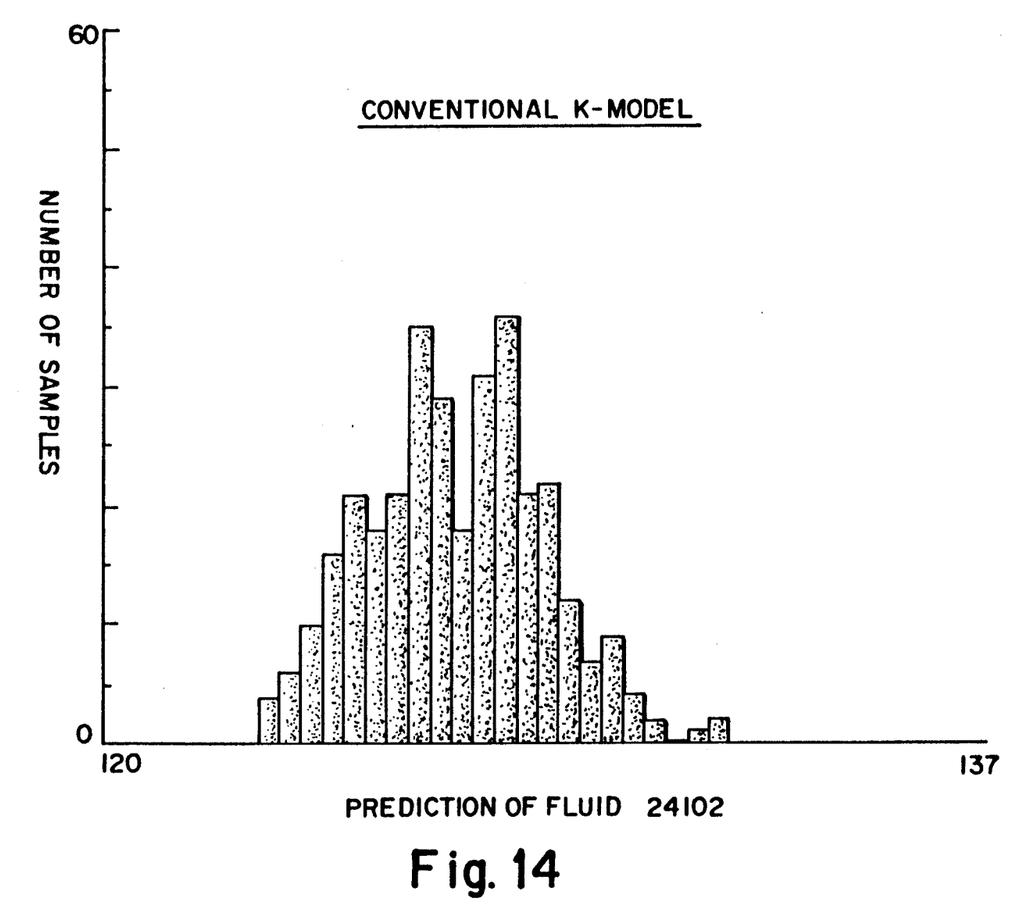
FIGS. 14–15 are plots of distributions of predictions of concentration using either the conventional K-Model method or the calibration method of the invention, respectively.

A calibration curve was found for each analyzer/coating combination using a conventional wet calibration protocol of 2 repetitions of each calibrator fluid. All repetitions of fluids, run on a given analyzer/coating combination, were predicted through that analyzer/coating combination's K-Model wet calibration curve. (Such "K-Model calibration is well known and is the method currently used in the "E400" TM and "E700" TM analyzers. FIG. 14 shows the distribution of these predictions for the control fluid, 24102, which is comprised of a human serum base pool with normal glucose concentration.. Analyzer 6 of the nine analyzers was used as the standard analyzer for the factory calibration model since this analyzer was a typical "E700" analyzer. Therefore, the K-Model wet calibration curve found for each coating on analyzer 6 served as the web characterization curve $F_{Lot}$, FIG. 13, for each coating. (All remaining analyzers are treated as "field analyzers".) Table 11 contains calibrator response information on coating 1 used in computing the analyzer characterizations.

TABLE 11

| Analyzer | Cal 1 Dr | Cal 2 Dr | Cal 3 Dr. |
|---|---|---|---|
| 1 | 0.32250 | 1.17297 | 1.58588 |
| 2 | 0.33128 | 1.18523 | 1.60577 |
| 3 | 0.33210 | 1.19432 | 1.59229 |
| 4 | 033587 | 1.19345 | 1.59562 |
| 5 | 0.33847 | 1.20931 | 1.62825 |
| 6 | 0.32895 | 1.18602 | 1.60482 |
| 7 | 0.33482 | 1.21462 | 1.63463 |
| 8 | 0.32409 | 1.17470 | 1.59108 |
| 9 | 0.31762 | 0.17360 | 1.58352 |

Since analyzer 6 was chosen as the standard, a quadratic function was found for each analyzer which converted the given analyzer's Dr to analyzer 6 Dr. The coefficients of the quadratic correction for each analyzer are listed in table 12.

TABLE 12

| Analyzer | $B_0$ | $B_1$ | $B_2$ |
|---|---|---|---|
| 1 | 0.00590 | 1.000057 | 0.005153 |
| 2 | −0.00595 | 1.012941 | −0.006120 |
| 3 | 0.01719 | 0.923388 | 0.046278 |
| 4 | 0.00662 | 0.948520 | 0.033277 |
| 5 | 0.00075 | 0.965598 | 0.012007 |
| 6 | 0.0 | 1.0 | 0.0 |
| 7 | 0.00997 | 0.946787 | 0.017671 |
| 8 | 0.00187 | 1.009693 | −0.001402 |
| 9 | 0.01693 | 0.977254 | 0.016108 |

To provide a factory calibration curve for coating 4 on "field" analyzer 8, the following two steps are used:

1. The analyzer 8 characterization is used to convert the Dr of the sample on analyzer 8 to the Dr of the sample on the standard analyzer, i.e., analyzer 6, using:

$$\text{Standard Dr} = 0.00187 + 1.009693 \cdot Dr + -0.001402 \, Dr^2$$

2. The K-Model calibration curve for coating 4 on the standard analyzer, i.e., analyzer 6, is used to convert standard Dr to concentration.

The factory calibration curves for all analyzer/coating combinations are constructed in a similar manner. If a markedly different generation of slide elements, e.g., of the "Ektachem" glucose elements, produces a drastically different correlation on the standard analyzer, new spline transformations will be then supplied to the field analyzers with that new generation of slide elements, for re-adjustment of the memory of the field analyzer. This is currently done by magnetic floppies for the "E700" and the "E400" analyzers manufactured by Eastman Kodak Co.

Figure 15:
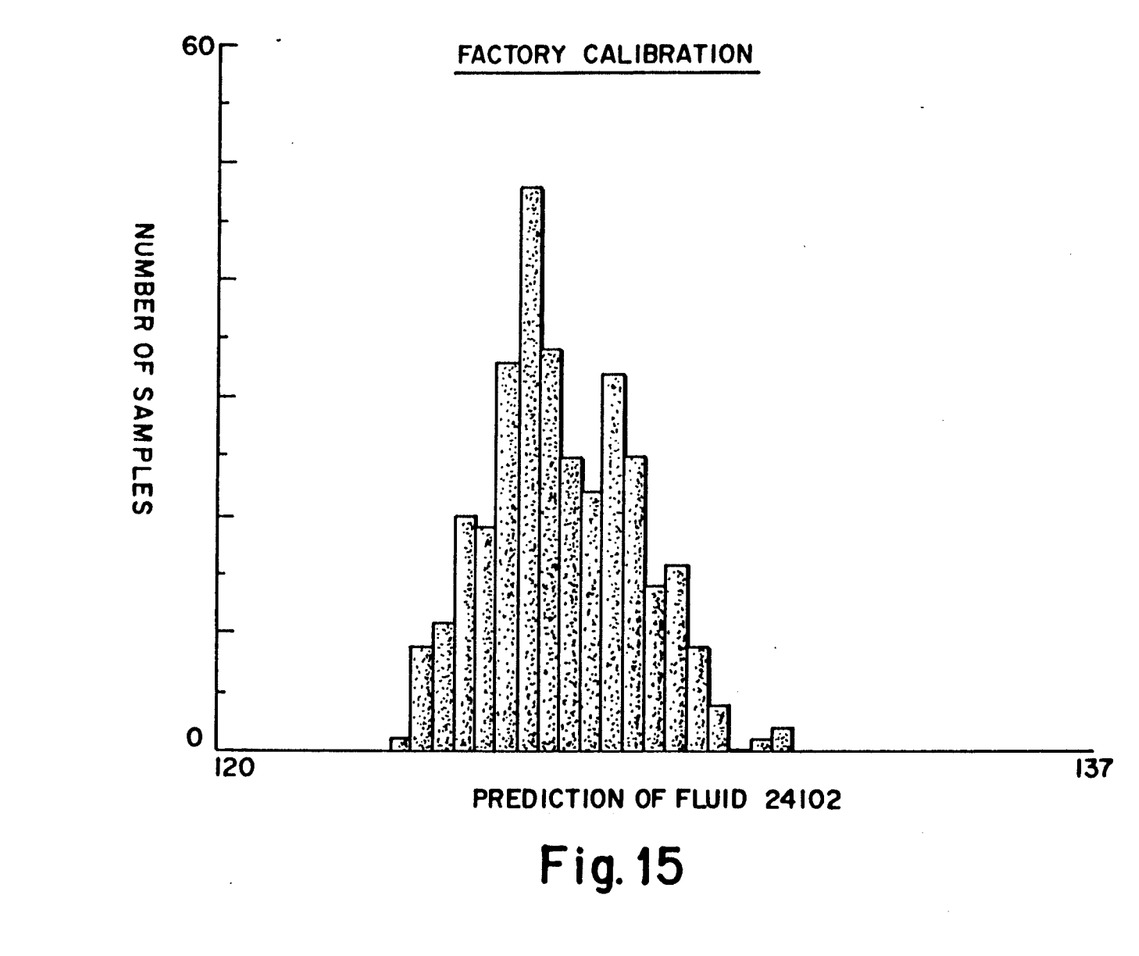

All repetitions of fluids run on a given analyzer/coating combination are predicted through that analyzer/coating combination's factory calibration curve. FIG. 15 shows the distribution of predictions for the control fluid 24102 using the factory calibration technique, that is, after converting the Dr readings on analyzer 8 as the "Field Response", left quadrant of FIG. 13, to "predicted Concentration" in the right quadrant.

VARIANCES

The variance of predicted concentration across all analyzer/coating combinations for the three controls and two patient pools are printed in table 13. "Kodatrol 1" "Kodatrol 2" are lyophilized human serum-based control fluids available under these trade names from the Eastman Kodak Co., and are included to illustrate the ability of the factory calibration to work with a variety of liquids.

TABLE 13

| Fluid | Concentration | K-Model Variance | Factory Calibration Variance |
|---|---|---|---|
| Kodatrol I | 88.31 | 1.84 | 1.53 |
| Kodatrol II | 303.33 | 7.32 | 7.04 |
| Control 24102 | 126.48 | 3.474 | 2.486 |
| Human Pool 1 | 60.04 | 0.697 | 0.566 |
| Human Pool 2 | 412.11 | 26.31 | 29.89 |

The variance of predicted concentration using the factory calibration of this invention is similar to the variance obtained when one uses the K-Model conventional three-level wet calibration method.

EXAMPLE 6

Factory Calibration of Amylase (Two-Point Rate)

This example used the following:

Nine "E700" analyzers from Eastman Kodak Co., which were intentionally varied to cause analyzer differences; five lots of "Ektachem" amylase slide elements from three different coatings; three calibrator fluids; three control fluids; and two patient pools.

Eight repetitions of each fluid were run on every analyzer/slide lot combination for a total of 360 (8×5×9) repetitions of each fluid.

The same control was used as for Example 5, that is, a calibration curve was found for each analyzer/slide lot combination using a conventional wet calibration protocol of 2 repetitions of each calibrator fluid. All repetitions of fluids, run on a given analyzer/slide lot combination, were predicted through that analyzer/slide lot combination's K-Model calibration curve.

In this example, analyzer 9 was used as the standard analyzer for the factory calibration since this analyzer was a typical "E700" analyzer. Therefore, the K-Model wet calibration curve found for each slide lot on analyzer 9 served as the web characterization curve $F_{Lot}$ for each lot. Since analyzer 9 was chosen as the standard, a quadratic function, Equation (I), was found for each analyzer which converted the given analyzer's rate to analyzer 9 rate.

To provide a factory calibration curve for slide lot 4 on "field" analyzer 8 the following two steps were used:

1. The analyzer 8 characterization was used to convert the rate of the sample on analyzer 8 to the rate of the sample on the standard analyzer, i.e., analyzer 9, using:

$$\text{Standard Rate} = B_0 + B_1 \cdot Rate + B_2 Rate^2$$

2. The K-Model calibration curve for slide lot 4 on the standard analyzer, i.e., analyzer 9, was used to convert standard rate to concentration.

The factory calibration curves for all analyzer/slide lot combinations are constructed in a similar manner.

All repetitions of fluids run on a given analyzer/slide lot combination were predicted through that analyzer/slide lot combination's factory calibration curve.

VARIANCES

The variance of predicted concentration across all analyzer/slide lot combinations for the three controls and two patient pools are printed in table 14.

TABLE 14

| Fluid | Concentration | K-Model Variance | Factory Calibration Variance |
|---|---|---|---|
| Kodatrol I | 83.27 | 16.31 | 24.96 |
| Kodatrol II | 370.30 | 1110.33 | 1273.48 |
| Control 24102 | 53.64 | 8.39 | 7.99 |
| Human Pool 1 | 706.31 | 974.10 | 993.70 |
| Human Pool 2 | 379.32 | 140.57 | 212.34 |

The variances of predicted concentration using the factory calibration model are only slightly greater than the variance obtained when one uses the conventional K-Model three-level customer wet calibration model.

CONCLUSIONS

This data shows that the factory calibration method of the invention yields results similar to the conventional K-model three-level customer calibration model for glucose and amylase. Similar test data can be shown for most other "Ektachem" slide element chemistries.

The invention has been described in detail with particular reference to preferred embodiments thereof, but it will be understood that variations and modifications can be effected within the spirit and scope of the invention.

What is claimed is:

1. In a method of quantitatively determining an analyte in a liquid sample applied to a slide element by measuring in a read station of a field analyzer a response developed in the slide element and correlating said response to an analyte concentration using a calibration curve produced from calibrators having known concentrations, such slide elements being selected from a set of slide elements that all produce the same response in said field analyzer except for deviations selected from the group consisting of lot-to-lot variations and aging, said same response being a function of the kind of analyzer used;

the improvement wherein said response on said analyzer is corrected substantially to the response that would have been detected on a standard analyzer of a type different from said field analyzer and having one of said calibration curves for correlating the response to an analyte concentration, by the steps of:

a) applying at least one level of said calibrators on at least one of said set of slide elements and reading the response in said standard analyzer, b) repeating step a) but by reading said response created in said field analyzer by said at least one level of calibrator;

c) correlating the relationship of the different responses in said two analyzers by using the equation (I):

$$R_{standard} = B_0 + B_1 \cdot g_F(R_F) + B_2 \cdot g_F(R_F)^k \qquad (I)$$

where $R_{standard}$ is the response detected in said standard analyzer, $R_F$ is the response detected in said field analyzer; $g_F(R_F)$ is a spline function used to transform the responses $R_F$; $B_0$, $B_1$ and $B_2$ are standardizing coefficients; and k is an exponent corresponding to the nonlinearity of the equation, d) incorporating said correlated relationship into said field analyzer so that it is available for use with an unknown patient liquid, e) applying an unknown patient liquid sample to a slide element selected from said set of slide elements and reading a response in said read station of said field analyzer;

f) ascertaining from said correlation of step c) what said read response in said field analyzer in step e) would produce as the corresponding response in said standard analyzer, and g) correlating said ascertained corresponding response to a predicted analyte concentration using said calibration curve of said standard analyzer.

2. A method as defined in claim 1, wherein said read response in the field analyzer is reflectance or optical density and said k of equation (I) is a value of 2.

3. A method as defined in claim 1, wherein said read response in the field analyzer is the rate of change of either R or OD or a transformed OD.

4. A method as defined in claim 1, wherein said step f) includes the further step of correcting for any deviation produced in said field analyzer due to aging variations so that said read response from said field analyzer corresponds to a standard fresh slide element of a type actually used in said step a).

5. A method as defined in claim 1, wherein said step f) includes the further step of correcting for any deviation produced in said field analyzer due to lot-to-lot variations so that said read response from said field analyzer corresponds to a standard fresh slide element of a type actually used in said step a).

6. A method as defined in claims 1 or 5, where said read response in the field analyzer is selected from the group consisting of reflectance R, optical density OD where $OD = \log(1/R)$; rate of change in R, OD and a transformed OD; and electrical potential created by a differential measurement of ion concentration in two ion-selective electrodes.

7. A method as defined in claim 1 or 5, wherein calibration math is provided as a set of machine-readable digits with each set of slide elements sent to any one of said field analyzers, that are suitable to establish for said one field analyzer the value of said coefficients $B_0$, $B_1$ and $B_2$.

8. A method as defined in claim 1 or 5, wherein said steps a), b) and c) are done at a manufacturing facility for said field analyzer and wherein said equation (I) is stored in memory in said field analyzer, so that said field analyzer is factory-calibrated and does not need field calibration.

* * * * *